Feb. 11, 1964 C. FISCHER Plant Pat. 2,362
GLADIOLUS PLANT
Filed Dec. 18, 1962
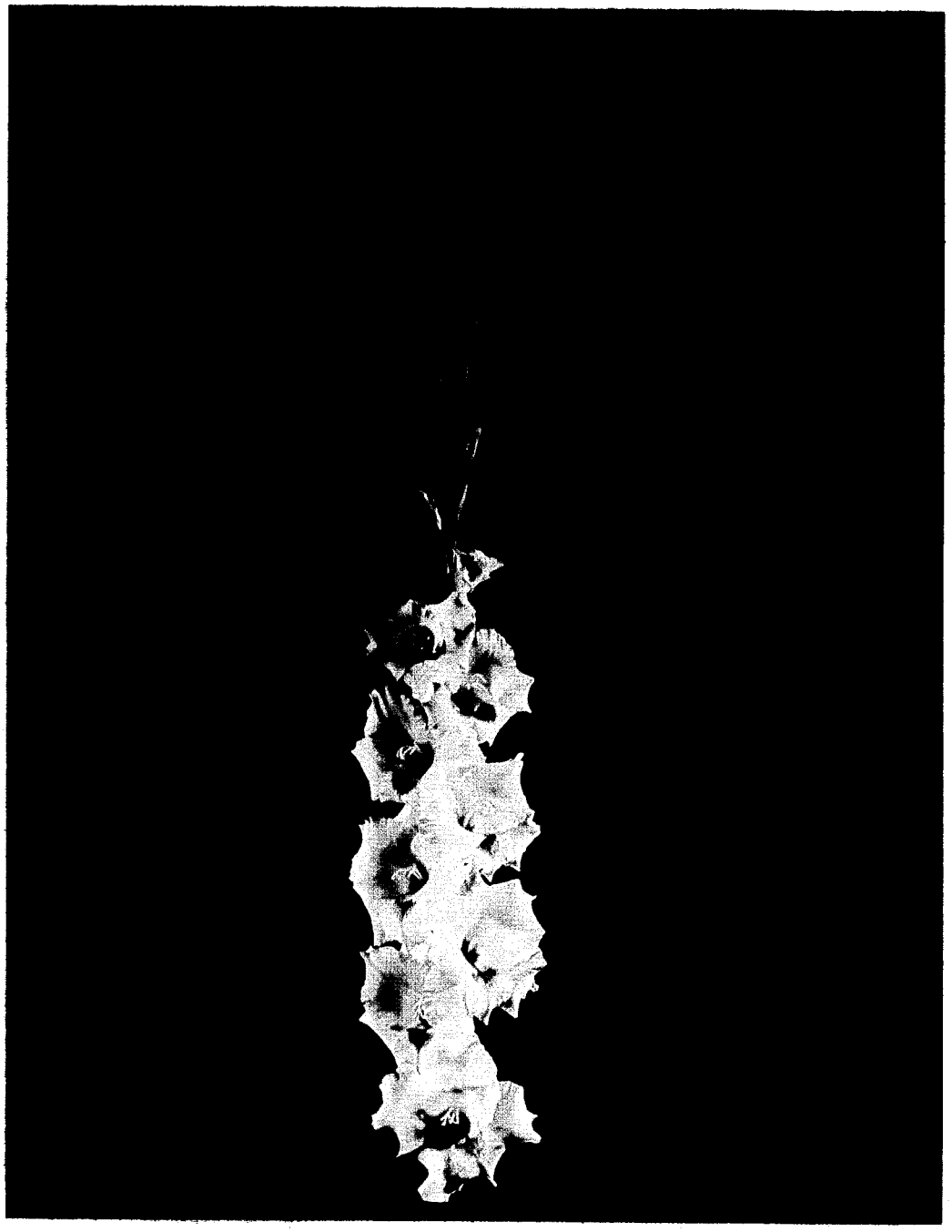
Inventor.
Carl Fischer
By: Robb & Robb
Attorneys.

United States Patent Office

Plant Pat. 2,362
Patented Feb. 11, 1964

2,362
GLADIOLUS PLANT

Carl Fischer, St. Charles, Minn., assignor to Imperial Flowers Limited, Leamington, Ontario, Canada, a corporation of Canada Filed Dec. 18, 1962, Ser. No. 245,631
1 Claim. (Cl. Plt.—85)

The present invention relates to a new and distinct variety of gladiolus plant which was originated by me by crossing the variety known as "Friendship" (unpatented) with the variety known as "Crusader" (unpatented), the former being the seed parent and the latter being the pollen parent. This cross was made by me by manual cross-pollination in my breeding fields at St. Charles, Minnesota, as a part of a breeding program seeking to obtain new and improved gladiolus varieties.

The primary objective of the aforementioned cross was to produce a superior white-flowered gladiolus variety in which the flowers are characterized by an attractive blotch contrasting with the basic white color. This objective was fully achieved, along with other desirable features, as evidenced by the following unique combination of characteristics which are outstanding in my new variety and which distinguish it from its parents, as well as from all other varieties of which I am aware:

(1) A rugged and vigorous habit of growth;
(2) Long flowerheads;
(3) An ability of the flowers to open well from tight buds;
(4) A distinctive and attractive white general color tonality of the flowers, combined with a sharp purple blotch;
(5) Good temperature tolerance; and
(6) Good disease resistance.

My new variety resembles the variety known as "Margaret Beaton" (unpatented) more than any other, but differs principally therefrom by a taller plant habit, longer flowerheads, a tendency of the flowerheads to arch forward slightly; more open florets, and greater temperature tolerance.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely rugged; slow propagator; average height ranges from about 60 inches to 64 inches.

Blooming habit: Mid-season bloomer in the Northern latitudes of the United States; comes into bloom from large bulbs in about 85 days; flowerhead bows forward at the tip.

Stem: Tall, willowy.
- *Diameter at base.*—About ⅜ inch.
- *Color (just above bulb).*—White.

Foliage: Healthy; upright; leaves average about 36 inches tall and range from about 1⅜ inches to 1½ inches wide. Color—green.

Disease resistance: Unusually good resistance to Fusarium yellows, Sclerotina dry rot and Septoria leaf spot, as determined by comparison with other varieties grown in my fields near St. Charles, Minnesota, in irrigated black loam soil.

Corms (bulbs): Heavy; plump; round; average diameter about 2 inches; well husked; very smooth. Color of flesh—Orange Buff, Plate 507/2.

*Flower*

Spike: Tall; bears from 18 to 20 buds, with from 6 to 8 buds opening at once, and with 5 or 6 additional buds showing color.

Bud:
- *Size.*—About 2½ inches long when opening.
- *Opening.*—Opens well; 5 or 6 buds show color at once; one of the best openers of all varieties formerly known.

Flower:
- *Arrangement.*—Florets are informally arranged on the stem, but almost always face forward.
- *Size.*—Lower florets average about 5 inches in diameter, with upper florets being progressively smaller.
- *Form.*—Florets are round, extremely recurved and somewhat needle-pointed.
- *Keeping qualities.*—Keeps well.

Petals:
- *Shape.*—Round; ruffled; recurved; somewhat needle-pointed; heavy midribs.
- *Size.*—Outer petals—from 2 inches to 2¼ inches wide. Lip petal—1¼ inches wide.
- *Aspect.*—Average substance; extremely smooth surface.
- *Fragrance.*—None.
- *Color.*—White, with blotch of Orchid Purple, Plate 31; blotch has prominent midrib of same shade.

*Reproductive Organs*

Stamens: Color—white.
Pistil: Color—white.

I claim:

A new and distinct variety of gladiolus plant, substantially as herein shown and described, characterized particularly as to novelty by the unique combination of a rugged and vigorous habit of plant growth, long flowerheads, an ability of the flowers to open well from tight buds, a distinctive and attractive white general color tonality of the flowers, with a sharply contrasting purple blotch, good temperature tolerance, and good disease resistance.

No references cited.